United States Patent
Green et al.

(10) Patent No.: US 6,617,349 B2
(45) Date of Patent: Sep. 9, 2003

(54) BLENDS OF ISOFLAVONES AND FLAVONES

(75) Inventors: Martin Richard Green, Sharnbrook (GB); Anne Hailes, Sharnbrook (GB); Maria Catherine Tasker, Sharnbrook (GB); Paula Rachel Yates, Sharnbrook (GB)

(73) Assignee: Lipton, division of Conopco, Inc., Englewood Cliffs, NJ (US)

( * ) Notice: Subject to any disclaimer, the term of this patent is extended or adjusted under 35 U.S.C. 154(b) by 0 days.

(21) Appl. No.: 09/930,525

(22) Filed: Aug. 15, 2001

(65) Prior Publication Data

US 2002/0068121 A1 Jun. 6, 2002

(30) Foreign Application Priority Data

Aug. 16, 2000 (EP) .............................. 00307031

(51) Int. Cl.$^7$ ........................ A61K 47/00; A61K 39/385
(52) U.S. Cl. ....................... 514/456; 424/439
(58) Field of Search ........................... 424/439; 514/456

(56) References Cited

U.S. PATENT DOCUMENTS

| | | |
|---|---|---|
| 5,498,631 A | 3/1996 | Gorbach et al. |
| 5,733,926 A | 3/1998 | Gorbach |
| 5,952,374 A | 9/1999 | Clarkson, Jr. et al. |
| 6,210,701 B1 * | 4/2001 | Darland et al. ............ 424/439 |

FOREIGN PATENT DOCUMENTS

| | | |
|---|---|---|
| DE | 100 09 424 | 9/2001 |
| WO | 98/08503 | 3/1998 |
| WO | 98/56373 A | 12/1998 |
| WO | 00/01351 | 1/2000 |
| WO | 00/07607 | 2/2000 |
| WO | 00/33824 A | 6/2000 |
| WO | 00/59523 A | 10/2000 |
| WO | 00/64276 | 11/2000 |
| WO | 01/64177 A1 | 9/2001 |

OTHER PUBLICATIONS

The Merck Index, 13$^{th}$ edition (2001), p. 1438, O'Neil, M., editor.
European Search Report dated Feb. 2, 2001.
XP 000979400 "Synergistic action of quercetin andgenistein in human ovarian carcinoma cells" vol. 9, No. 11–12, 1997, pp. 597–602.
XP 000979401 "Signal transduction and biochemical targeting of ovarina carcinoma" vol. 21, No. 3, 2000, pp. 231–236.

* cited by examiner

*Primary Examiner*—Frederick Krass
(74) *Attorney, Agent, or Firm*—Gerard J. McGowan, Jr.

(57) ABSTRACT

Blends of quercetin and isoflavones from the group consisting of genestein, daidzein and glycetin display synergistic effects when applied as anti-inflammatory agent or as skin agent in particular for anti ageing purposes.

15 Claims, 2 Drawing Sheets

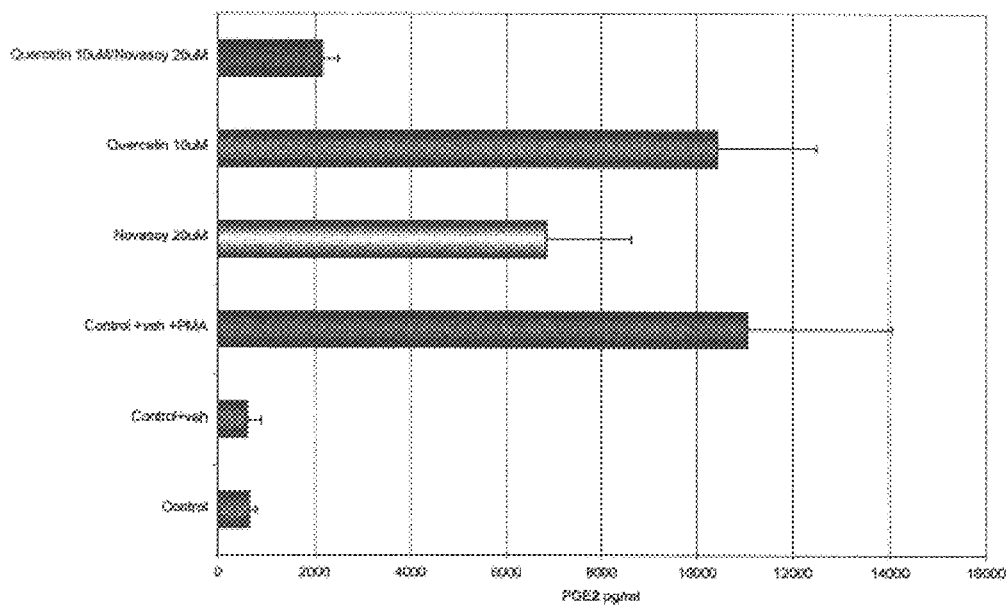

BLENDS OF ISOFLAVONES AND FLAVONES

Isoflavones are known as health components that can be applied to prevent or treat many health deficiencies or to achieve certain health effects not directly related with a health deficiency. E.g. these compounds are known to achieve benefits in the women's health area in particular for postmenopausal women. These effects are disclosed in e.g. U.S. Pat. No. 5,498,631; WO 98/ 56373; WO 98/08503; U.S. Pat. No. 5,733,167 926; U.S. Pat. No. 5,952,374 and many other references. Health effects that are also attributed to isoflavones include skin effects and anti-inflammatory effects.

Although for a few of these effects some experimental support can be found in the literature the majority of the pretended effects are mere statements in the prior art without any experimental support. We found on basis of a number of tests specifically developed in order to find experimental support to confirm the pretended effects that indeed some of the pretended effects exist however only to a low or medium extend.

Although WO 00/07607 discloses that a cancer-protective and cancer therapeutic composition is obtained by combining 1) a plant extract with antioxidant effect with
2) a neovascular regulator that inhibits angiogenesis and
3) with absorbable zinc whereas in the text the possibility of synergy between one or more of the components is suggested, there is no clear teaching that a synergy could be achieved by combining the components from which we found that they gave a synergy with respect to anti-inflammatory effects or with respect to skin benefits in particular to antiageing effects. In fact the preferred antioxidants are in this WO'607 bioflavanoids such as proanthocyanidins. The neovascular regulator can be genistein, daidzein or a soy isolate.

We therefore studied whether we could find ways wherein the existing effects in particular with respect to anti-inflammatory and to antiageing of the skin of the isoflavones could be enhanced. As a result of this study we found that this can be done in a synergistic way by combining the effects from a number of selected isoflavones with the effect of a specific flavone. In fact we found that by combining one or more of the isoflavones selected from the group consisting of genistein, daidzein and glycetin with quercetin (=a specific flavone) synergistic effects could be achieved that were far higher than could be expected on basis of the components present in the combination. Therefore our invention concerns in the first instance a blend of a synergistic mix of a natural flavone and natural isoflavones, wherein the flavone is quercetin and the isoflavones are selected from at least one of the isoflavones from the group consisting of genestein, daidzein and glycetin either in the glucon or in the aglucon form.

In these blends the weight ratios quercetin to isoflavone can vary over a wide range, however we found that the best results were obtained when weight ratios of 1:50 to 50:1, preferably ratios of 1:20 to 20:1, more preferably ratios of 1:6 to 6:1 and even more preferably from 1:4 to 4:1 and most preferably from 1:2 to 2:1, calculated as aglucon, were applied. Even better results were obtained by using weight ratios of 1:2 to 1:1.

The most preferred isoflavones in these compositions are genestein and daidzein (or as glucons the genistin and daidzin). Although these components can be applied in a wide range of ratios the best results were obtained, when the genistein and daidzein were used in weight ratios of 2:1 to 1:2.

The isoflavones and the quercetin that can be applied according to the invention are suitably derived from natural sources. Quercetin e.g. is present in onions, garlic and tomatoes and concentrates wherein this component is present in relatively high levels can be obtained from these sources. Very suitable sources for the isoflavones are soy flour or clover and in particular extracts from soy or clover with an increased content of isoflavones, these concentrates are available as commercial products.

The application of above teaching might result in a blend wherein the quercetin is present in amounts of 10 mg to 200 mg per RDI (recommended daily intake) while the isoflavones can be present in amounts of 10 mg to 200 mg per RDI. In this way the health components can be delivered as part of the daily servings of the food product.

According to another embodiment of our invention the invention also concerns food products containing a health component (=Functional food) wherein the food product comprises an amount of the blend of quercetin and at least one of the isoflavones genestein, daidzein and glycitin according to the invention, so that the total recommended daily intake (=RDI) of the health components is delivered by one to 5 servings per day of the food product.

Typically the food products can be selected from the group consisting of spreads, margarines, creams, sauces, dressings, mayonnaises, ice creams, fillings, confectioneries, health bars, cereals, health drinks.

In these food products 20 to 400 mg recommended daily intake of the synergistic blends according to the invention can be present. Because of the occurence of the synergy the food product can contain less of the individual flavone and iso-flavones, than otherwise would be required to achieve similar effects. In this way the performance of the food product is not negatively affected by the presence of the synergistic blend of health components while the health benefits are obtained.

In addition to the above components the blends and the food products can contain other micronutrients, examples thereof being anti oxidants (Vitamin C or Vitamin E), other vitamins in particular Vitamin B1, B6 and B12, Vitamin K, folic acid, minerals like calcium, magnesium, iron, copper, or zinc, however, emulsifiers also can be present as well as minor amounts of polyunsaturated fatty acids in particular DHA and EPA and in particular (deodorised) fish oils or concentrates thereof.

According to a last embodiment of our novel finding we also found that the blends or food products containing them can be used to achieve certain health effects, in particular certain cosmetical effects. Therefore our invention also concerns the use of a health composition comprising natural flavones and isoflavones wherein the health composition is the blend according to the invention or the food composition according to the invention and wherein the blend or food product is applied to achieve cosmetical effects, in particular skin benefits and skin related effects such as anti-ageing effects or for promoting the formation of collagen or for promoting the decorin formation in the skin. Further the invention concerns the use of a health composition comprising natural flavones and isoflavones wherein the health composition is the blend according to the invention and wherein the blend is applied for the production of a functional food with anti-inflammatory properties with a synergistic effect on the anti-inflammatory and related health properties.

This use can also result in a method for the treatment respectively the prevention of inflammations and related health deficiencies in animals or humans by administering to the animal or human in one or more servings in total an effective amount of the synergistic blend according to the invention or of the food product containing this blend according to the invention.

However the method can also comprise a method to achieve skin benefits or skin related effects, respectively to achieve the promotion of collagen formation or decorin formation in the skin by administering to an animal or human in one or more servings per day in total an effective amount of the synergistic blend according to the invention or the food product according to the invention.

In these methods for administering the amount to be administered should be the effective amount of the health component corresponding with the recommended daily intake of the isoflavones cq the flavone.

Procedure for Measuring Procollagen-I and Decorin Synthesis in Human Dermal Fibroblasts Preparation of Dermal Fibroblast Conditioned Medium Primary human foreskin fibroblasts at passage 2 (P2) were seeded into 12-well plates at 10,000 cells/cm$^2$ and maintained for 24 hours in atmospheric oxygen in Dulbecco's Modified Eagle Medium (DMEM) supplemented with 10% foetal calf serum.

After this time the cells were washed with serum free DMEM and then incubated in fresh serum free DMEM for a further 60 hours. Novasoy 40$^R$ containing 20 mM isoflavones, genistein, daidzein and glycetin (in a ratio of 1:1.3:0.3) and 5 mM quercetin were, either independently or in combination added to the cells in triplicate in a final volume of 0.4 ml/well fresh serum free DMEM and incubated for a further 24 hours. 1% ethanol was used as the vehicle control. This fibroblast conditioned medium was either analysed immediately or snap frozen in liquid nitrogen and stored at −70° C. for future analysis. The cells were then counted and data from the dot-blot analysis subsequently standardised to cell number.

Dot Blot Assay for Procollagen-I and Decorin Protein in Dermal Fibroblast Conditioned Medium Samples of conditioned medium from dermal fibroblasts treated with actives as listed above were supplemented with 20 mM dithiothreitol (1:10 dilution of 200 mM stock solution) and 0.1% sodium dodecylsulphate (1:100 dilution of 10% stock solution), mixed well and then incubated at 75° C. for 2 minutes. A standard for the assay was generated by serial dilution of neat fibroblast conditioned medium from fibroblasts seeded at 10,000 cells/cm2 in a 175 cm2 flask and maintained in serum free DMEM as described above.

Assay samples were subsequently applied in triplicate to a pre-wetted sheet of Immobilon-P transfer membrane using the 96-well Bio-Dot Apparatus from Bio-Rad as described in the manufacturers guidelines. Approximately 200 µl of medium was applied per well. The medium was allowed to filter through the membrane under gravity (30minutes) after which the membrane was washed twice with PBS (200 µl). These PBS washes were allowed to filter through the membrane under gravity (2×15 minutes). The Bio-Dot apparatus was then attached to a vacuum manifold and a third and final PBS wash carried out under suction. The apparatus was disassembled, the membrane removed and quickly cut as required before being placed in blocking buffer overnight at 4° C.

Membranes prepared for procollagen-I and decorin analysis were both blocked with 5% (w/v) non fat dried milk powder/0.05% Tween 20 in PBS. The following day, the membranes were probed with 1:10000 dilution of primary antibodies to either human procollagen-I (MAB1912; rat monoclonal; Chemicon Int. Inc., Temecula, Calif.) or human decorin (mouse polyclonal; AMS, UK) for 2 hours at room temperature. The membranes were subsequently washed with TBS/ 0.05% Tween 20 (3×5 minutes) and then incubated with 1:1000 dilution of 125I-conjugated anti-rat or anti-mouse F(ab')2 fragments (ICN, Amersham respectively) as required for 1 hour at room temperature.

Following this the Immobilon strips were again washed with TBS/Tween 20 (3×5 minutes) before being allowed to dry in air at room temperature. The dried membranes were wrapped in cellophane and exposed to a Molecular Dynamics storage phosphor screen for 16–18 hours. At the end of this time the exposed screen was scanned by a phosphorimager (Molecular Dynamics Phophorimager SF) using ImageQuant™ software. Dot intensity was assessed by computer-assisted image analysis using quantification tools in ImageQuant™, standardised to cell number and the effects of various test reagents on decorin and procollagen-I synthesis were determined relative to a vehicle treated control value of 100 arbitrary units.

BRIEF DESCRIPTION OF THE DRAWINGS

FIG. 2 illustrates the synergistic interaction of quercetin and Novasoy 40 when combined at concentrations of 10 µm and 20 µm.

RESULTS

Figure 1:
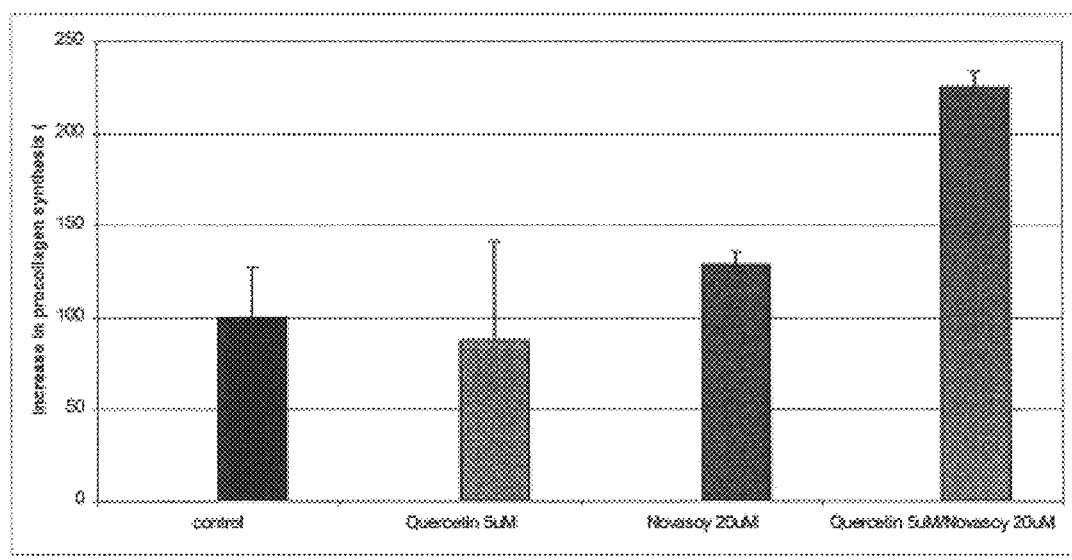
FIG. 1 illustrates the synergistic interaction of quercetin and Novasoy 40 when combined at concentrations of 5 µm and 20 µm.

When quercetin and Novasoy 40 are added to cells at sub-optimal concentrations (i.e. those concentrations just below the concentrations that produce maximal upregulation of procollagen-1) the synthesis of procollagen-1 can be enhanced when quercetin and Novasoy 40 are combined at concentrations of 5 uM and 20 uM (isoflavones), respectively. A synergistic interaction was observed between Novasoy 40 and quercetin when they were combined at the above concentrations. (cf. FIG. 1)

Fibroblasts PGE$_2$ Assay

PGE$_2$ production by human skin fibroblasts can be induced by the inflammatory stimulus PMA (phorbal myristate acetate). PMA represents and external stressor which induces oxidative stress and inflammatory responses in cells. This model is used to model inflammation in vivo.

Primary human foreskin fibroblasts at passage 2 (P2) were seeded into 96-well plates at 35,000 cells/well and maintained for 24 hours in an atmosphere of 5% carbon dioxide in Dulbecco's Modified Eagle Medium (DMEM) supplemented with 10% foetal calf serum. Novasoy 40 ® containing 20 mM isoflavones, genistein, daidzein and glycetin (in a ratio of 1:1.3:0.3) and 5 mM quercetin were either independently or in combination added to the cells (DMEM, supplemented with 10% foetal calf serum) in dimethylsulphoxide (ethanol, final concentration 1%) in triplicate and incubated for a further 24 hours. Phorbal myristate acetate (PMA) (Sigma) was added to the media and the cells incubated for a further 24 hours. The control did not contain any test compounds nor any PMA. The fibroblasts/media were then analysed immediately or snap frozen in liquid nitrogen and stored at −70° C. for future analysis. The cells were then counted and data from the dot-blot analysis subsequently standardised to cell number.

Prostaglandin E2 (PGE$_2$) assay: Volumes of 50 μl culture medium were taken for PGE$_2$ assay after gently shaking the culture plate. PGE$_2$ levels in the medium were determined with a Biotrak PGE$_2$ immunoassay kit (Amersham, UK). The assay is based on the competition between unlabelled PGE2 in the sample and a fixed quantity of horseradish peroxidase labeled PGE$_2$ for a limited amount of fixed PGE$_2$ specific antibody. Concentrations of unlabeled sample PGE$_2$ are determined according to a standard curve, which was obtained at the same time.

When quercetin and Novasoy 40 are added to cells at sub-optimal concentrations (i.e. those concentrations just below the concentrations that produce maximal down-regulation of PGE2) the down-regulation of PGE2 can be enhanced when quercetin and Novasoy 40 are combined at concentrations of 10 uM and 20 uM (isoflavones), respectively. A synergistic interaction was observed between Novasoy 40 and quercetin when they were combined at the above concentrations. (cf. FIG. 2)

EXAMPLE

RECIPE 3.4 grams of vegetable fat 0.5 g of modified egg yolk together named "creamer"

6.0 g of maltodextrin 0.025 grams of Novosoy 40 ® containing 40 wt % of the isoflavones genistin/daidzin and glycitin in a weight ratio of 1.3:1:0.3

0.010 grams of quercitin 0.6 grams of maize starch croutons 16.1 grams of dried potato starch 1.0.grams of salt 0.3 grams of onion solids 0.7 grams of onions 0.2 grams of parsley and herb extract 3.2 grams of flavouring agents The creamer and the other components are mixed in mixer The blend obtained is a dried instant onion soup that can be used for making a soup by mixing it with 200 ml of boiling water under stirring. The soup that is made this way tastes very well.

What is claimed is:

1. A blend comprising a synergistic mix of a natural flavone and natural isoflavones, wherein the flavone is quercetin and the isoflavones are selected from the group consisting of genestein, daidzein and glycetin either in the glucon or in the aglucon form and wherein quercetin and the natural isoflavones are present in a weight ratio of 1:50 to 50:1, calculated as aglucon, and genestein and daidzein are present in a weight ratio (as aglucon) of 2:1 to 1:2.

2. The blend according to claim 1 wherein the weight ratio of quercetin to total isoflavones ranges from 1:2 to 2:1.

3. The blend according to claim 1 wherein the weight ratio of quercetin to genestein (as aglucon) ranges from 1:2 to 1:1.

4. The blend according to claim 1 wherein the quercetin is a natural product derived from onions or from garlic or from tomatoes.

5. The blend according to claim 1 wherein the natural isoflavones are derived from soy.

6. The blend according to claim 1 wherein the quercetin is a concentrate of onions, or of garlic or of tomatoes.

7. The blend according to claim 1 wherein the blend contains 10 mg to 200 mg of quercetin and 10 mg to 200 mg of the isoflavones.

8. A food product comprising the blend according to claim 1.

9. The food product according to claim 8, wherein the food product is selected from the group consisting of spreads, margarines, creams, sauces, dressings, mayonnaises, ice creams, fillings, confectioneries, health bars, cereals, and health drinks.

10. The food product according to claim 8 wherein the food product contains 20 mg to 400 mg of the synergistic blend.

11. A method for treating inflammation or health deficiencies in animals or humans by administering to the animal or human an effective amount of the blend according to claim 1.

12. A method for promoting collagen formation or decorin formation in skin by administering to an animal or human an effective amount of the blend according to claim 1.

13. A method according to claim 11 wherein the effective amount is the recommended daily intake.

14. The blend according to claim 5, wherein the natural isoflavones comprise soy flour or soy extracts.

15. The blend according to claim 5, wherein the natural isoflavones are soy extracts having an enhanced isoflavone content.

* * * * *